(12) United States Patent
Droche

(10) Patent No.: US 11,458,043 B2
(45) Date of Patent: Oct. 4, 2022

(54) DRESSING FOR SKIN CARE IN A MOIST ENVIRONMENT

(71) Applicant: Emile Droche, La Garenne-Colombes (FR)

(72) Inventor: Emile Droche, La Garenne-Colombes (FR)

( * ) Notice: Subject to any disclaimer, the term of this patent is extended or adjusted under 35 U.S.C. 154(b) by 765 days.

(21) Appl. No.: 16/060,688

(22) PCT Filed: Dec. 9, 2016

(86) PCT No.: PCT/EP2016/080468
§ 371 (c)(1),
(2) Date: Jun. 8, 2018

(87) PCT Pub. No.: WO2017/097993
PCT Pub. Date: Jun. 15, 2017

(65) Prior Publication Data
US 2018/0360667 A1    Dec. 20, 2018

(30) Foreign Application Priority Data
Dec. 9, 2015   (FR) ....................... 1562074

(51) Int. Cl.
*A61F 13/02*   (2006.01)
*A61F 13/00*   (2006.01)
*A61K 9/70*    (2006.01)

(52) U.S. Cl.
CPC .. *A61F 13/00068* (2013.01); *A61F 13/00063* (2013.01); *A61F 13/023* (2013.01);
(Continued)

(58) Field of Classification Search
CPC .......... A61F 13/00068; A61F 13/00063; A61F 13/0216; A61F 13/0226; A61F 13/023;
(Continued)

(56) References Cited

U.S. PATENT DOCUMENTS 3,171,410 A  *  3/1965  Towle, Jr. ............ A61B 17/135
                                                602/53
3,367,332 A     2/1968  Groves
(Continued)

FOREIGN PATENT DOCUMENTS

CA    2586948 A1    5/2006
CN    1121309 A     4/1996
(Continued)

OTHER PUBLICATIONS

International Search Report PCT/EP2016/080468 dated Feb. 17, 2017 w/English language translation.
(Continued)

*Primary Examiner* — Camtu T Nguyen
(74) *Attorney, Agent, or Firm* — Fishman Stewart PLLC

(57) ABSTRACT

Dressing for skin care, having a main compress covered by a membrane with an adhesive contour which extends beyond this compress and which is designed to be applied to the skin, this dressing having an inlet port for a treatment liquid on the main compress, and the membrane having, on at least part of the surface opposite this compress, a permeability that permits exchange of gases.

20 Claims, 4 Drawing Sheets

(52) U.S. Cl.
CPC ...... *A61F 13/0216* (2013.01); *A61F 13/0226* (2013.01); *A61K 9/7084* (2013.01); *A61F 2013/00157* (2013.01); *A61F 2013/00174* (2013.01); *A61F 2013/00182* (2013.01); *A61F 2013/00285* (2013.01); *A61F 2013/00846* (2013.01); *A61F 2013/00855* (2013.01)

(58) Field of Classification Search
CPC .. A61F 2013/00157; A61F 2013/00174; A61F 2013/00182; A61F 2013/00285; A61F 2013/00846; A61F 2013/00855; A61K 9/7084
See application file for complete search history.

(56) References Cited

U.S. PATENT DOCUMENTS

| | | | | |
|---|---|---|---|---|
| 4,754,750 | A | * | 7/1988 | Imonti ................. A61F 15/008 D24/189 |
| 5,690,610 | A | * | 11/1997 | Ito ..................... A61F 13/0203 602/56 |
| 6,169,224 | B1 | | 1/2001 | Heinecke et al. |
| 9,561,134 | B2 | | 2/2017 | Scholz et al. |
| 2004/0073151 | A1 | * | 4/2004 | Weston ............ A61F 13/00068 602/41 |
| 2006/0079852 | A1 | * | 4/2006 | Bubb ................. A61M 1/0027 604/317 |
| 2007/0032755 | A1 | * | 2/2007 | Walsh ................. A61M 27/00 602/2 |
| 2014/0276475 | A1 | | 9/2014 | Taylor |
| 2015/0174304 | A1 | * | 6/2015 | Askem ................. A61M 1/732 604/319 |

FOREIGN PATENT DOCUMENTS

| | | |
|---|---|---|
| CN | 103813766 A | 5/2014 |
| WO | 9421207 A2 | 9/1994 |
| WO | 00/74616 A1 | 12/2000 |
| WO | 2013/039713 A2 | 3/2013 |
| WO | 2013039713 A2 | 3/2013 |
| WO | 2017097993 A1 | 6/2017 |

OTHER PUBLICATIONS

Translation—International Preliminary Report—PCT/EP2016/080468, dated Dec. 9, 2016.

* cited by examiner

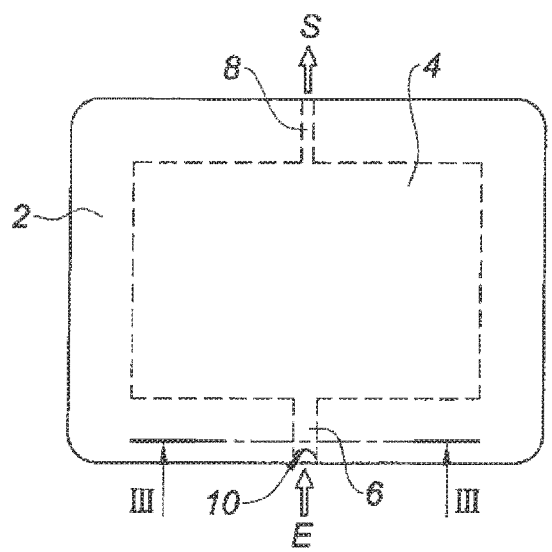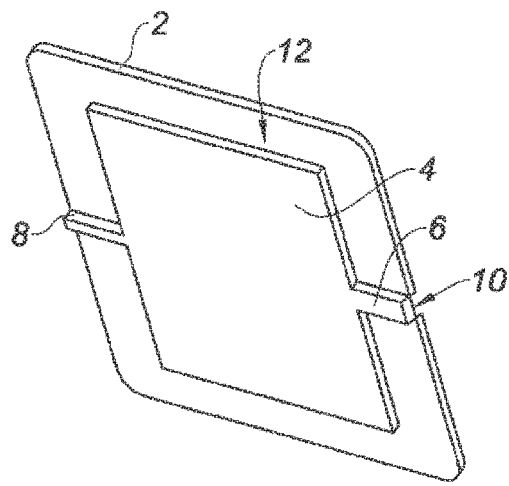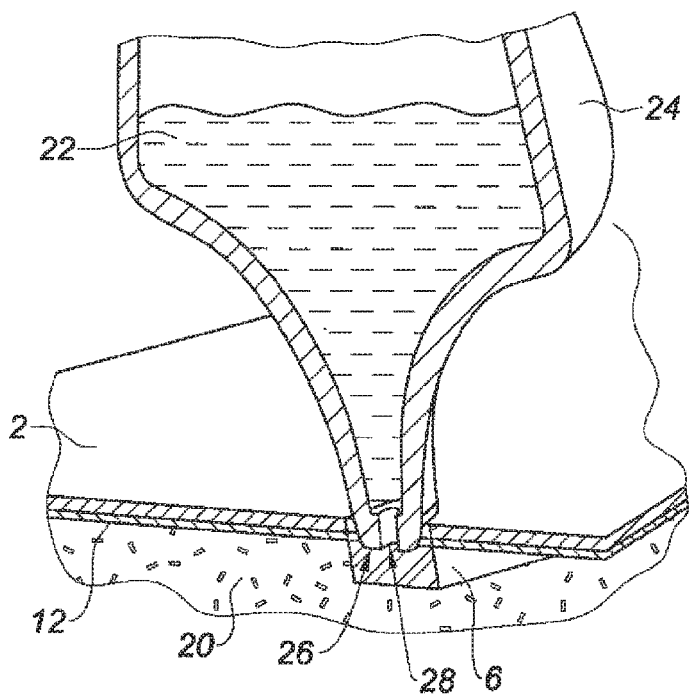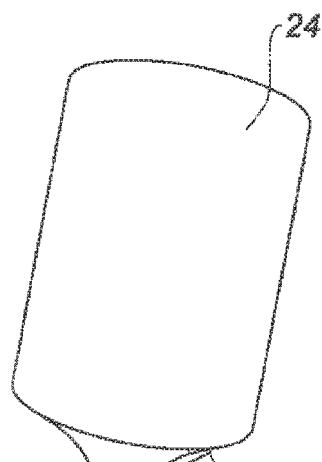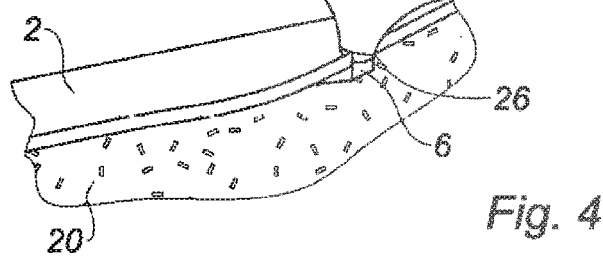
Fig. 1
Fig. 2
Fig. 3
Fig. 4

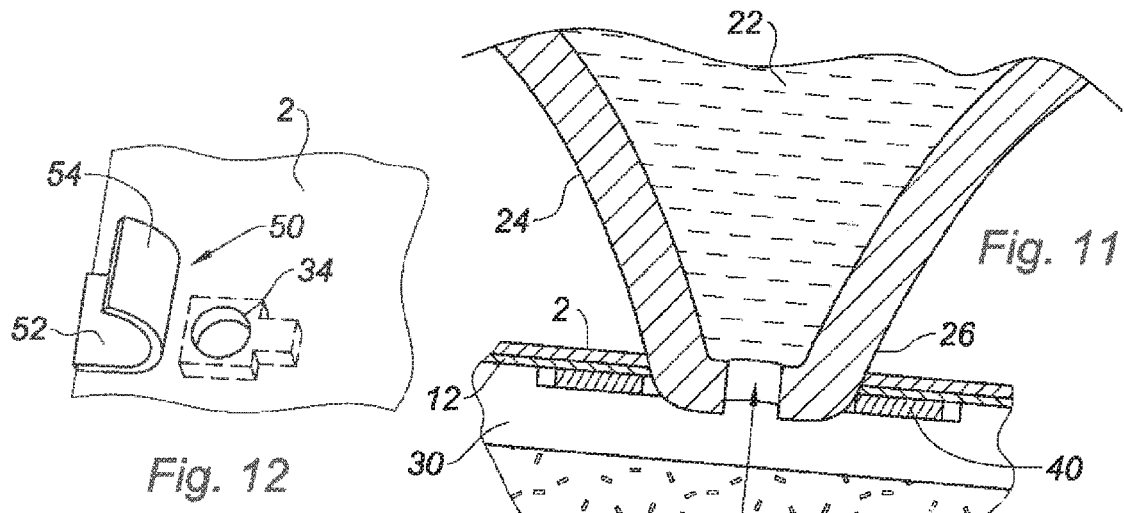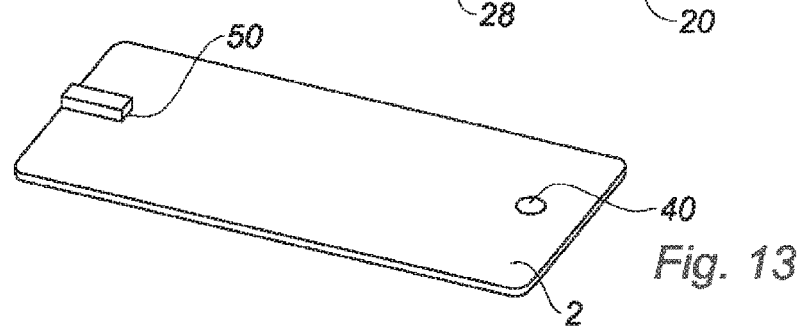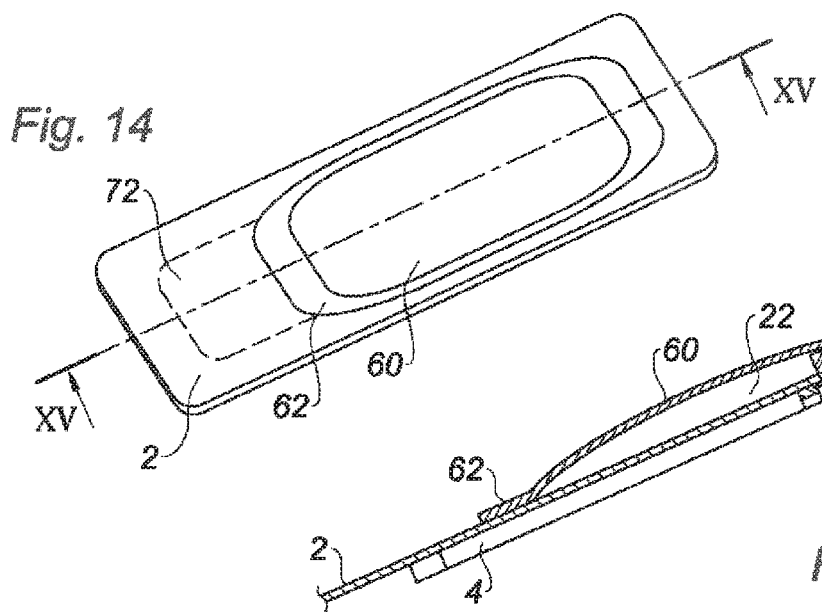

DRESSING FOR SKIN CARE IN A MOIST ENVIRONMENT

CROSS-REFERENCE TO RELATED APPLICATIONS

This is the U.S. National Stage of PCT/EP2016/080468, filed Dec. 9, 2016, which in turn claims priority to: French Application No. 1562074, filed Dec. 9, 2015, the contents of each of these applications being incorporated herein by reference in their entireties.

The present invention concerns a dressing system designed to be applied to the skin of a patient while maintaining a moist environment, as well as a method of using this dressing.

The current dressing which has been used for a long time now, includes a product forming a compress, which is covered by a film or a membrane whose contours are adhesive for applying this compress to the skin.

The primary function of this type of dressing is to protect a superficial wound on the skin of a patient by covering it to keep the wound dry and shielded from the external environment that can affect it. This protection which is to be changed several times a day is maintained for a period of time necessary to obtain a sufficient cicatrization of the skin.

This type of dressing which is economical is still used. It can have a slight antiseptic function to prevent infection of the wound, thus allowing longer intervals between changes, which are done, for example, once a day.

The wound may be caused by a variety of problems, including, in particular, a cut, a burn, a pustule, an ulcer or a skin disease.

A problem presenting itself with this type of dressing is that there are usually adhesions of the cicatrization tissue on the compress in the process of it being formed on the wound, such tissue then being torn loose during subsequent removal. The cicatrization cycle is thus slowed, and healing delayed. In particular, healing of ulcers may become impossible.

To limit adhesion of the compress, it is known to utilize, opposite the wound, a polymer grille and/or a product of the hydrocolloid type, which may be associated with vaseline. However, this solution is not always entirely satisfactory.

A currently proposed upscale type of dressing, which is more costly, promotes the cicatrization while maintaining a moist environment by means of a hydrocolloid mass.

Furthermore, some of these dressings can absorb bleedings. In that case, this type of dressing has to be replaced several times in the course of the treatment, generally for the first time after 24 hours, and then every 48 hours.

A special therapy realizes a negative pressure in the dressing maintaining a moist and antiseptic environment, in order to specifically promote the absorption of products by the skin. It is known to utilize different types of pump for creating a negative pressure; however, these systems entail elevated costs, and necessitate energy for the actuation of the pump.

As a variant, a type of dressing maintaining a negative pressure in a moist environment, presented in particular in document US-A1-20050070835, has a flat reservoir designed to be maintained on the dressing, containing chemical or electrochemical means which absorb oxygen in order to reduce the gas pressure in this reservoir.

However, this type of means designed to absorb oxygen is complex to use, and increases costs.

The object of the present invention is, in particular, to obviate these drawbacks of the prior art.

To this end, the invention proposes a dressing for skin care, having a main compress covered by a membrane with an adhesive contour which extends beyond this compress and is designed to be applied to the skin, this dressing being remarkable in that it has an inlet opening for a treatment liquid on the main compress, and in that the membrane, on at least part of the surface opposite this compress, has a permeability allowing exchange of gases.

An advantage of this dressing is that, on the one hand, the inlet port permits control of a flow rate of the treatment liquid for soaking the compress, and that, on the other hand, the permeability of the membrane to gas permits, during use of the dressing, to allow gases to escape in order to avoid pressure in this dressing. Moreover, the gas exchange makes it possible to avoid maceration of the wound and to renew the liquid.

The dressing according to the invention can furthermore have one or more of the following features, which can be combined with each other.

According to an embodiment, in addition to the permeability, the dressing includes an outlet port for the air contained in the main compress.

In particular, the inlet or outlet port can comprise a compress arm extending from a side of the main compress to traverse the adhesive contour. This type of inlet or outlet can be simply and economically realized.

As a variant, the inlet or outlet port can form a bore of the membrane, provided on the adhesive contour at a distance from the edge of this membrane.

In this case, advantageously, the bore of the inlet or outlet port has under the membrane a piece of compress which is separated from the main compress. The separation effects some degree of restraint of the flow, which imposes a supply pressure for obtaining the outflow of the liquid.

Advantageously, the membrane has an inlet bore, while a ring, for example rigid, is disposed under this membrane around this bore for realizing a centering of a tip for pouring liquid. Thus, in a simple manner, there is realized a tactile means for finding the bore as well as an aid for positioning of the tip.

Advantageously, the dressing has a means of closing the inlet port, comprising a flexible part which comes to lie on this opening. Thus, the inlet is protected from soiling.

Advantageously, the permeability allowing exchange of gases is formed by a microstructure or microperforations of the membrane.

According to an embodiment, the dressing has an integrated reservoir designed for receiving the liquid. In that case, there is no need to utilize an additional means for effecting the filling of the liquid.

In particular, the integrated reservoir can be formed by a tight upper sheet, fixed by its contour on the membrane or on a tight lower sheet which itself is fixed on the membrane.

Advantageously, the dressing with integrated reservoir has a valve for opening the reservoir towards the main compress, controlled by a knob. The knob permits a simple and easy control of the port of the reservoir to effect the infiltration of the compress.

Advantageously for a dressing with integrated reservoir, the membrane does not have an outlet in addition to the permeability. With the integrated reservoir allowing a slow compress impregnation flow by capillarity, the gas exchange permeability of this compress is sufficient to remove air contained within.

The invention further has for its object a method for treatment of a problem on the skin of a patient, which includes applying to the skin a dressing comprising any one of the foregoing features, and then impregnating the main compress with the liquid.

The invention will be better understood and other features and advantages will be apparent more clearly upon reading the description given below by way of example, with reference to the appended drawings in which:

FIG. 1 is a top plan view of a dressing according to the invention;

FIG. 2 is a bottom view of this dressing;

FIG. 3 is a sectional view taken along the line III-III of a bottle filling this dressing with liquid;

FIG. 4 is an exterior view of this bottle filling the dressing;

FIG. 11 is an axial sectional view taken along the line X-X of a bottle filling with liquid a similar dressing having a guiding ring;

FIGS. 12 and 13 are views respectively of a detail and of the whole of a similar dressing having a tongue for closing the inlet bore shown open, then closed;

FIGS. 14 and 15 show a dressing comprising an integrated liquid reservoir, seen respectively from above and in a section along the line XV-XV;

Figure 5:
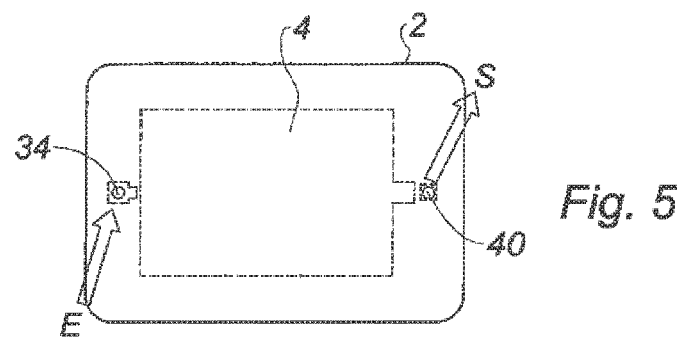
FIG. 5 is a top plan view of a dressing according to a first variant.
Figures 6, 7, 8:
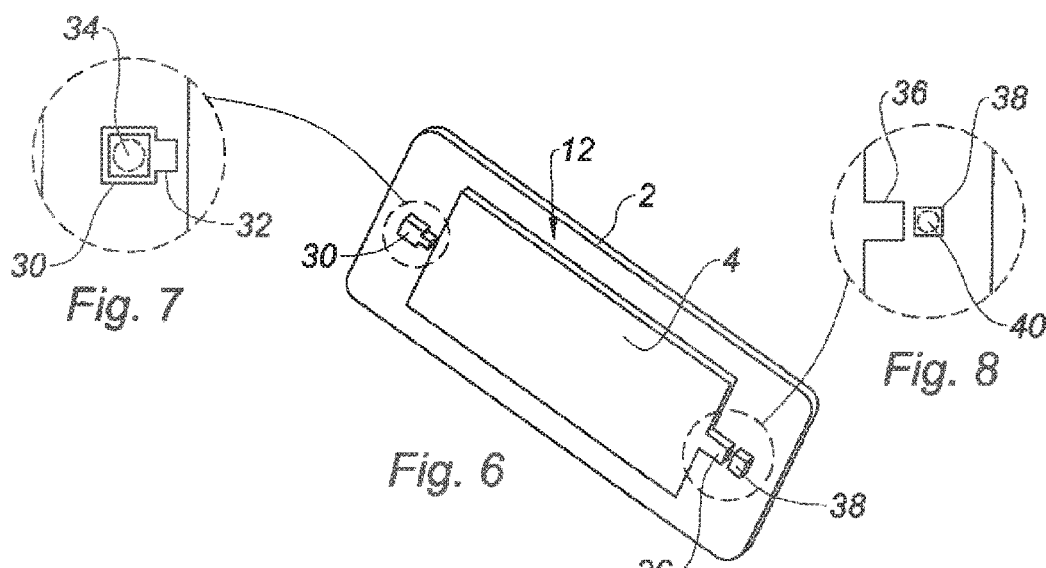
FIG. 6 is a bottom view of this dressing.
FIGS. 7 and 8 are detailed views of, respectively, the inlet and the outlet of this dressing.

FIGS. 1 and 2 show a dressing of rectangular shape, including an outer flexible membrane 2 receiving thereunder a flat compress 4 which is surrounded by a border of the membrane of constant width receiving a self-adhesive adhesive coating 12.

The membrane 2, at least on the surface opposite the compress 4, has a permeability that permits exchange of gases, by means of, for example, a microstructure or microperforations.

Advantageously, the membrane 2 is made of plastic, in particular, use can be made of a polyurethane which is flexible and economical.

On a side of the rectangle, the compress 4 continues by way of an inlet arm 6, extending up to the outer contour of the membrane 2, terminating in a concave circular arc 10 which is also cut out on the membrane. On the opposite side, the compress 4 continues by way of an outlet arm 8 having a reduced width.

Once applied to the skin, the adhesive coating 12 of the membrane 2 encloses the contour of the compress 4 entirely, except for the ends of the inlet arm 6 and outlet arm 8 which remain accessible from the outside.

FIGS. 3 and 4 show a bottle 24 containing a treatment liquid 22, having a narrowing tip 26 terminating in a rounded portion having an axial bore 28.

Once the dressing has been applied to the skin, the operator adjusts the tip 26 of the bottle 24 on the concave, circular-arcuate cutout 10 of the compress inlet arm 6 and of the membrane 2, and injects the liquid 22 with a slight pressure, for instance by pressing on the bottle which is of flexible plastic, to propel it by capillarity into the inlet arm 6 and then into the whole compress 4.

During this injection, the air contained in the closed volume formed under the membrane 2, filled by the compress 4, is driven out on the other side via the outlet arm 8 which is permeable to this air.

In particular, by providing a transparent or translucid membrane 2, the advance of the liquid through the compress 4 can be followed, and complete filling can be verified. Further, a colored liquid may be provided which allows its advance to be followed more easily.

Fill-up of the dressing can also be ascertained on the evidence of an outflow of liquid via the outlet arm 8, which would demonstrate complete fill-up. The orifices of inlet 6 and outlet 8 moreover permit an outflow of liquid, during use of the dressing, to obviate a rise of pressure inside upon an incidental compression of the dressing, for example in the case where the dressing sits on a joint of a limb which is bent.

Additionally, some time after initial filling up of the dressing, it is possible, proceeding in the same manner, to effect a replenishment with the same liquid, or a different liquid in the course of the progress of the treatment, to compensate for any evaporation or slight liquid seepage.

The reduced section of the outlet arm 8 relative to that of the inlet arm 6 is adapted to allow an outflow of air which easily proceeds through a small cross section, whereas the cross section of the inlet for the liquid is larger.

In addition to an outlet of gas through the outlet arm 8, any gas production in the dressing is evacuated in a simple manner on the whole surface of this compress via the gas permeability of the membrane 2.

The reduced cross section of the inlet and outlet orifices at the ends of the arms 6, 8 limits the possibility of entry of bacteria into the dressing. Moreover, these inlet and outlet orifices are spaced from the main compress 4 by the length of the arms 6, 8, which limits the possibility of migration of bacteria towards this compress.

There is obtained a compress impregnated with a liquid which is confined on the wound, containing, at least at the outset, an antiseptic. The composition of the liquid may evolve during the treatment. The dressing can be preserved a great deal longer due to the possibility of recharging with liquid.

In particular, it is possible, with the same dressing, to implement cutaneous or transcutaneous treatments that involve an evolution of the medicinal products utilized. This type of treatment is of particular interest for taking care of lesions such as aphthae, pustules, ulcers, allergies, or for reducing scars.

During removal of the dressing, maintenance of the whole wound surface in a moist environment strongly limits regenerated tissues adhering and being torn loose. In addition, replenishment of the liquid makes for longer preservation of the dressing which is changed less often, which also reduces the risk of these tissues being torn loose.

Use can be made of any type of reservoir for the poured into liquid, including in particular bottles of plastic or glass, ampoules or syringes.

FIGS. 5, 6, 7 and 8 show a dressing forming an elongated rectangle, comprising a similar compress 4 surrounded by a border receiving the adhesive coating 12.

On a short side of the rectangle, the border receives thereunder an inlet system spaced from the contour of the membrane 2, comprising a square piece of inlet compress 30 having on a side facing the main compress 4 a spike 32 separated from this compress by a small distance. The membrane 2 has an inlet bore 34 provided at the center of the square piece of inlet compress 30.

On the opposite short side of the rectangle, the border receives thereunder an outlet system comprising an arm 36 connected with the compress 4, and, at a small distance from its end, a square piece of outlet compress 38 which is at a distance from the contour of the membrane 2. The membrane 2 has an outlet bore 40 provided at the center of the square piece of outlet compress 38.

In this manner, after application of the adhesive coating 12 on the skin, there are obtained inlet and outlet compress pieces 30 and 38, respectively, which are spaced from the edges of the membrane so as to provide a tightness of these pieces relative to the outside.

Also, as a result of the small distance without compress on the inlet and the outlet, there is obtained an restrained passage between the main compress 4 and this inlet or outlet, which allows a passage of liquid only in the case where a certain pressure is applied. By simple capillarity there is no passage of liquid obtained.

Figures 9, 10:
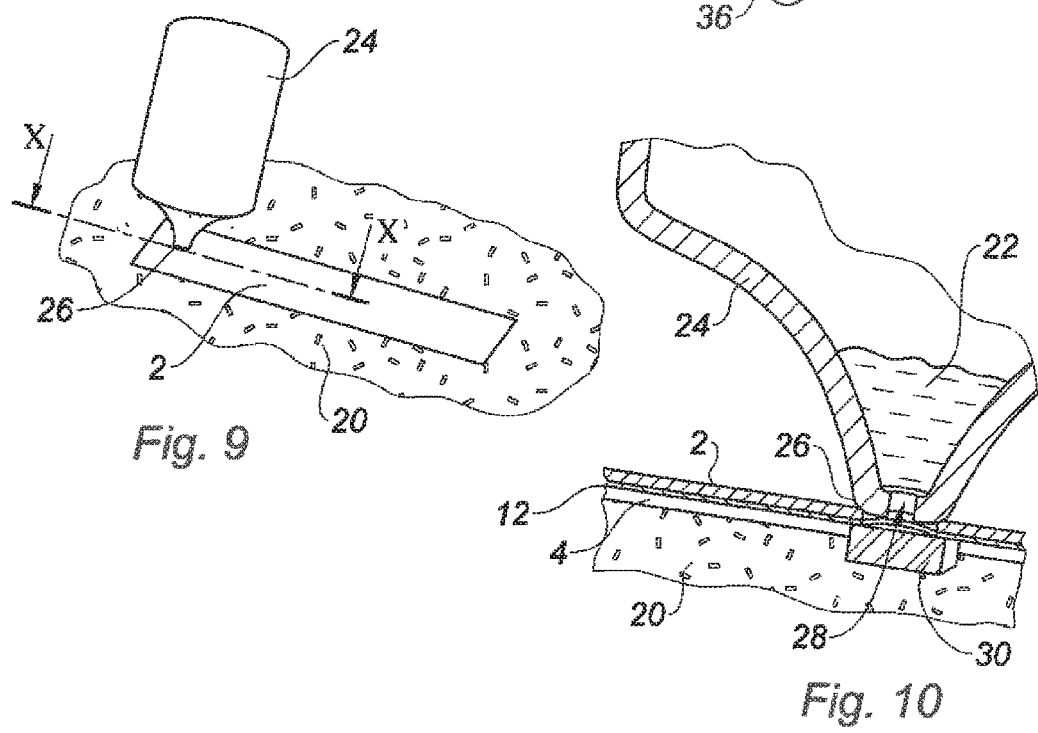
FIG. 9 is an exterior view of a bottle filling this dressing.
FIG. 10 is a sectional view taken along the line X-X of a bottle filling this dressing with liquid.

FIGS. 9 and 10 show the application of the narrowing tip 26 of the bottle 24 on the inlet bore 34, which makes it possible, while applying a pressure on the liquid 22, for instance by pressing the bottle which is flexible, to obtain an impregnation of the inlet compress piece 30, which communicates via the spike 32 and via the small distance separating it from the main compress 4, towards this compress to soak it entirely.

It will be noted that, with the inlet bore 34 receiving the end of the narrowing tip 26 which is lodged inside, there is obtained an easy centering of this tip which comes directly into contact with the inlet compress piece 30, which limits the losses of liquid towards the outside.

In a similar manner, the air contained in the compress 4 is driven towards the outlet arm 36, then passing via the small distance, towards the outlet compress piece 38 communicating with the outlet bore 40.

The small distances without compress on the inlet and the outlet also allow liquid to be received from the compress when it is saturated and compressed by flexure of a joint, for example.

The inlet pressure necessary due to the restrained passage of the liquid on the inlet makes it possible to limit any infiltrations of other fluids towards the compress 4, in particular if the inlet and outlet systems are emptied, as well as of the migration of bacteria through the compress, which protects it from soiling or from infections.

In addition, with the respective inlet and outlet compress pieces 30 and 38 being spaced from the edges of the membrane 2, there is a continuity of adhesion of this membrane throughout its circumference, resulting in an absence of risk of propagation of any detachment starting from an inlet or outlet passage that would extend up to this edge.

FIG. 11 shows a dressing similar to that presented in the foregoing, having in addition a guiding washer or ring 40, for example rigid, which is disposed around the inlet bore 34, between the membrane 2 and the compress 4, which is bonded under said membrane by way of the adhesive coating 12.

The guiding ring 40 having a central bore aligned with the inlet bore 34 constitutes a means of centering the narrowing tip 26 of the bottle 24, allowing this tip to be positioned and maintained on a rigid part, so as to effect a transfer of the liquid 22 with avoidance of any shifting of the bottle which would cause a loss of this liquid.

Moreover, the guiding ring 40 facilitates locating the position of the bore 34 for a visually impaired person, this piece being perceptible by a touch through the membrane 2.

FIGS. 12 and 13 show a similar dressing, having in addition a closing strip 50 with an end 52 stuck to the membrane 2 in proximity to the inlet bore 34, the other end forming a flexible part 54 to be arranged on the inlet bore to keep it closed.

In this manner, the inlet bore 34 is permanently kept closed to protect it from contaminations, and by a simple raising of the flexible part 54, the bore is uncovered for a supply of the dressing with liquid.

Figure 16:
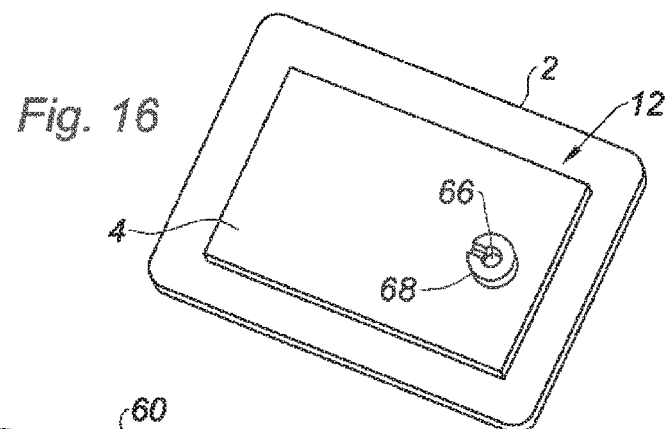
FIG. 16 shows this dressing seen from below.

FIGS. 14, 15 and 16 show a dressing comprising on top of the membrane 2 an integrated reservoir formed by a tight, flexible sheet of plastic 60 fixed by its contour 62 on the membrane. In particular, the sheet 60 may be fixed on the membrane 2 by a glued joint, in particular with a polyurethane glue, or by a welded joint, in particular with a high-frequency weld.

A reservoir-opening valve 66 is disposed on the main median axis of the dressing, on a side of the reservoir 60, in order to allow a passage of the liquid from this reservoir towards the compress 4.

The contour 62 of the sheet of reservoir 60 leaves free, on the side opposite to the valve 66, on top of the compress 4, a free part 72 of the membrane 2 which is uncovered in order to allow, through its permeability to gas, an exit of gases contained in this compress.

In this manner, there is obtained during the impregnation of the compress 4 a flux of liquid coming from the valve 66 which progressively soaks this compress by capillarity whilst progressing along the main axis of the dressing, and driving ahead of it the air which is displaced towards the opposite edge where is the membrane's free part 72 allowing the evacuation of gases.

Figure 17:
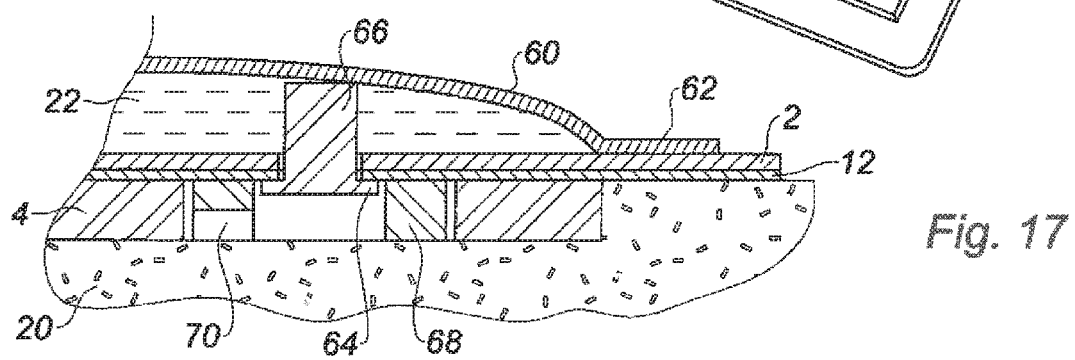
FIGS. 17 and 18 are sectional views taken along the line XV-XV, of this reservoir with an valve for opening shown in closed and open position respectively.
Figure 18:
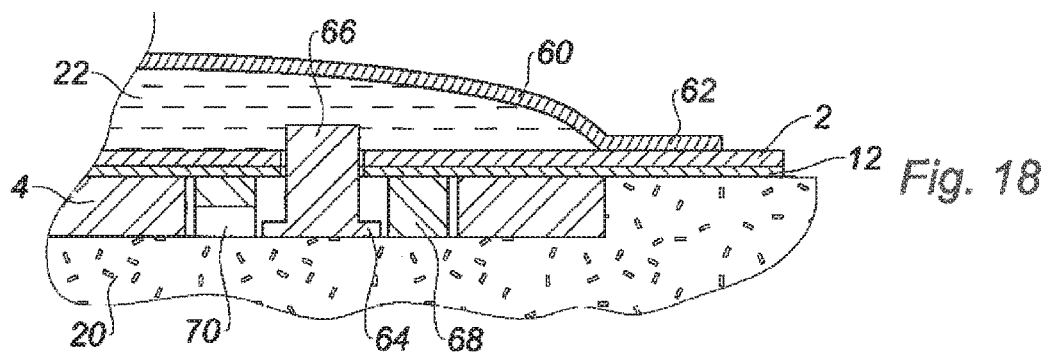

FIG. 17 shows in detail the valve 66 comprising a cylindrical knob traversing a bore of the membrane 2, whose top is set to be under the flexible sheet 60 of the filled reservoir. The base of the cylindrical knob of the valve 66 forms a circular shoulder 64 which is initially bonded under the membrane 2 by way of the adhesive coating 12, in order to ensure a tightness sealing the reservoir.

The shoulder 64 of the valve 66 is surrounded by a rigid ring 68 suitably fitted within the compress 4 and having at least the same thickness, comprising towards the bottom a horizontal channel 70 traversing this ring.

After having lodged the dressing on the skin of the patient 20, pressing the knob of the valve 66, through the flexible sheet 60, detaches the shoulder 64 from the membrane 2. The rigid ring 68 permits the descent of the valve 66 due to the vertical space it defines under the valve. Thus, a passageway of the liquid 22 to the compress 4 via the channel 70 is obtained.

In contrast to the bottle set up on the dressing presented hereinabove, which necessitates a transfer of the liquid by an operator who cannot spend all too much time, the reservoir integrated on the dressing allows the impregnation of the compress 4 to be effected for a long time, with a progressive flow of the liquid through the valve 66. The air contained in the compress 4 can then flow out progressively through the membrane's free part 72, without necessity for a specific outlet bore.

There is obtained an autonomous dressing not having any opening to the outside, the inlet of the liquid towards the compress 4 being integrated in the interior of the reservoir, which gives it a high level of protection from soiling and infections.

The treatment of the patient is simplified, with a single operation of applying the dressing to the skin, which can be done rapidly by lower-qualified staff, which reduces costs. The autonomous dressing with integrated reservoir does not necessitate any supplementary equipment, provision being made in particular for supply of dressings having a reservoir already filled with treatment liquid.

As a variant, provision can also be made for dressings supplied with an empty reservoir, where filling is done via an inlet plug, or by injection with a syringe through the flexible sheet 60.

Figure 19:
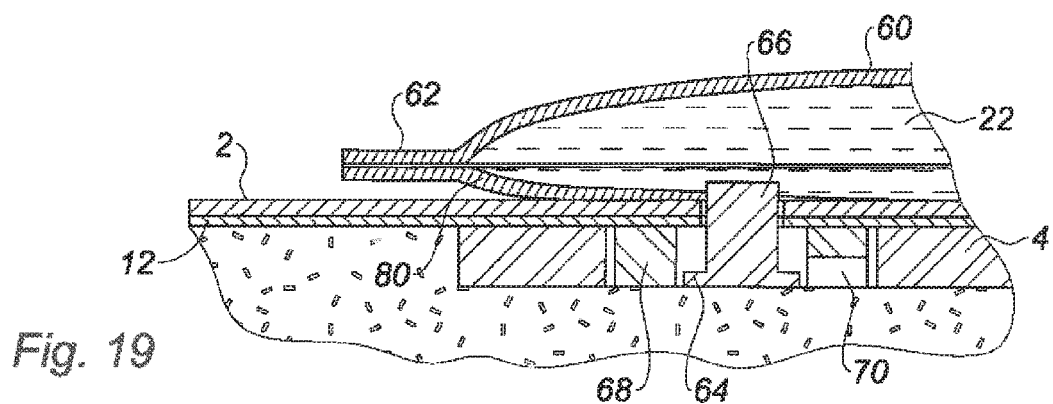
FIG. 19 is a sectional view taken along the same line XV-XV of a dressing having a reservoir according to a variant.

FIG. 19 shows a similar dressing, having a reservoir formed by a flexible upper sheet 60 which is fixed at its circumference to a flexible lower sheet 80. A central part of the lower sheet 80 has a bore tailored to fit the valve 66, the contour of the bore being adhered to the membrane 2 so as to ensure the passage of the liquid to this valve with a tightness all-around.

In closed position, the top of the valve 66 is set to be under the upper sheet 60 of the reservoir, the functioning of this valve being identical.

Generally, the dressing according to the invention allows a non-surgical treatment of a considerable variety of wounds or problems of the epidermis, comprising a rapid healing due to the presence of a moist environment receiving treatment products, and to the keeping in pace on the wound of this dressing for a sufficiently long time without any problem of adhesion of the regenerated tissues, which obviates their being torn loose.

The invention claimed is:

1. A dressing for skin care, having a main compress covered by a membrane with an adhesive contour which extends beyond the main compress and is adapted to be applied to skin, and having an inlet port for a treatment liquid on the main compress, the membrane comprising, on at least part of a surface opposite the main compress, a permeability that permits exchange of gases;
    wherein the inlet port comprises a compress arm extending from a side of the main compress to traverse the adhesive contour.

2. The dressing according to claim 1, including, in addition to the permeability, an outlet port for air contained in the main compress.

3. A dressing for skin care, having a main compress covered by a membrane with an adhesive contour which extends beyond the main compress and is adapted to be applied to skin, and having an inlet port for a treatment liquid on the main compress, the membrane comprising, on at least part of a surface opposite the main compress, a permeability that permits exchange of gases;
    wherein the inlet port comprises a compress arm extending from a side of the main compress to traverse the adhesive contour; and
    wherein the outlet port comprises a compress arm extending from a side of the main compress to traverse the adhesive contour.

4. A dressing for skin care, having a main compress covered by a membrane with an adhesive contour which extends beyond the main compress and is adapted to be applied to the skin, and having an inlet port for a treatment liquid on the main compress, the membrane comprising, on at least part of the surface opposite the main compress, a permeability that permits exchange of gases;
    wherein the inlet port forms a bore of the membrane, provided on the adhesive contour at a distance from an edge of the membrane.

5. The dressing according to claim 4, including, in addition to permeability, an outlet port for air contained in the main compress, the outlet port forming a bore of the membrane, provided on the adhesive contour at a distance from the edge of the membrane.

6. The dressing according to any one of claims 4 and 5, wherein the bore of the inlet port and/or the outlet port comprises under the membrane a piece of compress which is separated from the main compress.

7. The dressing according to any one of claims 4 and 5, wherein a rigid ring is disposed under the membrane, around the entry bore, to realize a centering of a tip for pouring liquid.

8. The dressing according to any one of claims 4 and 5, comprising an integrated reservoir designed to receive the liquid, the integrated reservoir communicating with the bore of the inlet port.

9. The dressing according to claim 8, wherein the integrated reservoir has a tight upper sheet fixed by its contour on the membrane or on a tight lower sheet which itself is fixed on the membrane.

10. The dressing according to claim 8, comprising a valve for opening of the reservoir towards the main compress, controlled by a knob, the knob traversing the bore of the inlet port.

11. The dressing according to claim 8, wherein the membrane does not have an outlet port in addition to permeability.

12. The dressing according to any one of claims 1, 2, 3, 4, and 5, comprising a closing member for closing the inlet port, comprising a flexible part coming to lie over the inlet port.

13. The dressing according to any one of claims 1, 2, 3, 4, and 5, wherein the permeability permitting exchange of gases is formed by a microstructure or microperforations of the membrane.

14. A set comprising a liquid reservoir and a dressing according to any one of claims 1, 2, 3, 4, and 5.

15. The dressing according to claim 6, wherein a rigid ring is disposed under the membrane, around the entry bore, to realize a centering of a tip for pouring liquid.

16. The dressing according to claim 6, comprising an integrated reservoir designed to receive the liquid, the integrated reservoir communicating with the bore of the inlet port.

17. The dressing according to claim 9, wherein:
    the dressing comprises a valve for opening of the reservoir towards the main compress, controlled by a knob, the knob traversing the bore of the inlet port; and/or
    the membrane does not have an outlet port in addition to permeability.

18. The dressing according to claim 10, wherein the membrane does not have an outlet port in addition to permeability.

19. The dressing according to claim 6, wherein:
    the dressing comprises a closing member for closing the inlet port, and a flexible part coming to lie over the inlet port; and/or
    the permeability permitting exchange of gases is formed by a microstructure or microperforations of the membrane.

20. The dressing according to claim 7, wherein:
    the dressing comprises a closing member for closing the inlet port, and a flexible part coming to lie over the inlet port; and/or the permeability permitting exchange of gases is formed by a microstructure or microperforations of the membrane.

\* \* \* \* \*